United States Patent [19]

Wong et al.

[11] Patent Number: 5,021,337

[45] Date of Patent: Jun. 4, 1991

[54] NON-INTRUSIVE PROCESS FOR MONITORING THE PRODUCTION OF RECOMBINANT PROTEINS

[75] Inventors: Patrick T. T. Wong; Saran A. Narang, both of Ottawa; Wing L. Sung, Gloucester, all of Canada

[73] Assignee: National Research Council of Canada, Ottawa, Canada

[21] Appl. No.: 219,306

[22] Filed: Jul. 15, 1988

[51] Int. Cl.$^5$ .............................................. C12Q 1/02
[52] U.S. Cl. ...................................... 435/29; 435/4; 435/18; 435/68.1; 435/69.1; 435/71.1; 435/71.2
[58] Field of Search .................. 435/29, 38, 69.1, 71.2

[56] References Cited
PUBLICATIONS

Nichols et al.—J. of Microbiological Methods, vol. 4 (1985), pp. 79–94.

*Primary Examiner*—Sam Rosen

[57] ABSTRACT

A process is described for monitoring the production of recombinant proteins. It is based on the discovery that infrared spectra of *E. coli* strains and transformants which overproduce recombinant proteins can be measured as a function of pressure, and a pressure-induced distinct shifting pattern can be observed in specific spectral parameters of transformants. In particular, the difference in the pressure-induced shift of the amide III band, between the *E. coli* cells and the transformants over-producing the recombinant proteins provides an efficient and non-intrusive technique for on-line monitoring of the production of recombinant proteins in *E. coli*.

8 Claims, 2 Drawing Sheets

NON-INTRUSIVE PROCESS FOR MONITORING THE PRODUCTION OF RECOMBINANT PROTEINS

BACKGROUND OF THE INVENTION

This invention relates to recombinant protein production and, more particularly, to a high pressure, infrared spectroscopic technique for monitoring such recombinant protein production.

The production of many prokaryotic and eukaryotic proteins in *Escherichia coli* has been made possible through the use of recombinant DNA technology. High-level expression of these proteins has been achieved by cloning their coding sequences into multi-copy plasmids downstream from strong promoters and ribosome binding sites to create recombinant expression plasmids. Using this approach, several investigators have reported that products of cloned genes can accumulate in certain cases up to 50% of total *E. coli* cell protein.

It has been observed that high level expression of these cloned genes resulted in the formation of insoluble proteinaceous aggregates. Also, many of the proteins may be found in the soluble fractions. It has, for instance, been found recently that the rapid degradation of human proinsulin synthesized in *E. coli* by recombinant DNA techniques can be prevented by inserting a DNA sequence encoding a short homooligopeptide, such a $(Ala)_6$, $(Asn)_6$, $(Cys)_7$, $(Gln)_7$, $(His)_6$, $(Ser)_6$ and $(Thr)_6$, at the 5' end of the proinsulin gene. The expressed polypeptide is then accumulated as cytoplasmic inclusion bodies, with the yield of proinsulin ranging between 6% and 26% of the total bacterial protein.

For large scale production of proinsulin and other proteins, an efficient method for direct determination of maximum gene expression and detection of any biological contamination would be important economically. However, the established procedures of radioimmunoassay and SDS-polyacrylamide gel electrophoresis are time-consuming, and therefore totally inappropriate as a monitoring process for commercial production.

SUMMARY OF THE INVENTION

According to the present invention, it has been found that infrared spectra of *E. coli* strains and transformants which overproduce recombinant proteins can be obtained as a function of pressure. Thus, according to the present invention high pressure infrared spectra of live bacteria have been successfully obtained.

It has been found that under ambient conditions, spectra of the host strain of *E. coli* and the transformants are generally identical. However, under pressure, a distinct shifting pattern can be observed in specific spectral parameters of transformants. This shifting pattern is observed in both cells producing inclusion aggregates of proteins and cells producing soluble proteins.

For instance, using the technique of the invention, infrared spectra of *E. coli* strain JM103 and transformants which overproduced recombinant proinsulin have been obtained as a function of pressure up to 38 kbar. Under pressure, distinct shifting patterns were observed in specific spectral parameters of transformants, and this is believed to be due to accumulation of proinsulin in the form of cytoplastic inclusion bodies. In particular, the pressure-induced frequency shift of the amide III band (1235 cm$^{-1}$) in the proinsulin-production transformants is much smaller than in the host JM103.

Further studies on lysozyme produced by the same recombinant protein technique have shown that they can also be monitored by the characteristic pressure-induced shift of recombinant proteins according to the present invention. Moreover, it has been found that this characteristic pressure-induced shift exists not only in cells producing inclusion aggregates of proteins, but also exists in cells producing soluble recombinant protein.

For carrying out the infrared spectrographic technique of the present invention, the material to be examined is placed in a sample holder to which high pressures of many atmospheres may be applied. Then, while applying a high pressure of, e.g. many atmospheres, to the sample, it is subjected to infrared spectroscopic analysis. The result is a pressure-induced shift in the infrared spectral parameters indicative of differences in cells tested.

It has been found that with this technique it is now possible to monitor the production of recombinant proteins in *E. coli*. In particular, it provides an efficient and non-intrusive on-line technique for determining when the genes in the *E. coli* sample have reached the maximum expression and the recombinant protein has been accumulated. Thus, the technique of this invention is uniquely adapted for use in commercial processes for the production of recombinant proteins. It is particularly unique in its ability to monitor the production of soluble proteins.

Calibration curves can be developed for selected recombinant proteins by conducting infrared spectroscopic measurements on each protein at varying pressures. These curves, which are preferably obtained from the frequency shift of the amide III band, indicate the maximum expression for each protein. Thus, in commercial production, samples of the recombinant protein can be very quickly tested at a fixed pressure at regular intervals until an infrared reading is obtained indicative of the desired overproduction of recombinant protein.

The actual pressure being applied to a sample can easily be determined by adding a small amount of powdered quartz to the sample and measuring the pressure from the infrared absorption band of quartz. This technique is described in Wong, P. T. T., Moffatt, D. J. and Baudais, F. L. (1985) Appl. Spectrosc. 39, 733–735, incorporated herein by reference.

According to a preferred feature, bacterial pellets centrifuged from a culture medium are placed within a diamond anvil cell. The cell is closed and tightened to apply pressure on the sample and an infrared spectrum is taken. This infrared spectrum provides both the frequencies for the pressure-indicating quartz band and the protein band. By comparison of the frequency of the protein band with that in a calbration curve at the corresponding pressure, the degree of completeness of the protein production is indicated.

Other features and objects of the present invention will be more fully understood from the following detailed description which should be read in the light of the accompanying drawings.

DETAILED DESCRIPTION OF THE PREFERRED EMBODIMENTS

Example 1

Proinsulin is synthesized in *E. coli* strain JM103 by known recombinant DNA techniques to obtain the *E. coli* strain and two transformants containing aggregates of proinsulin fused with either a $(Ala)_6(B)$ or a $(Asn)_6(C)$ leader.

*E. coli* pellets were obtained after centrifugation from culture medium. The bacterial pellets were placed together with powdered α-quartz in a 0.37 mm diameter hole on a 23 mm thick stainless steel gasket mounted on a diamond anvil cell as described above. Pressures on the samples were determined from the 695 cm$^{-1}$ infrared absorption band of quartz. Frequencies of this band were obtained from third power derivative spectra, calculated using a breakpoint of 0.3 in Fourier domain. Pressures were calculated from these frequencies according to the expression $P(kbar) = a_1\Delta\nu + a_2\Delta\nu^2$, where $\Delta\nu$ is the measured frequency shift, $a_1 = 1.2062$ and $a_2 = 0.015164$.

Infrared spectra of the samples were measured at 28° C. on a Bomen model DA3.02 Fourier transform spectrometer with a liquid nitrogen cooled mercury cadmium telluride detector. The infrared beam was condensed by a sodium chloride lens system onto the sample in the diamond anvil cell. The spectral resolution was 4 cm$^{-1}$, and typically 1000 scans were co-added for each spectrum.

Figure 1:
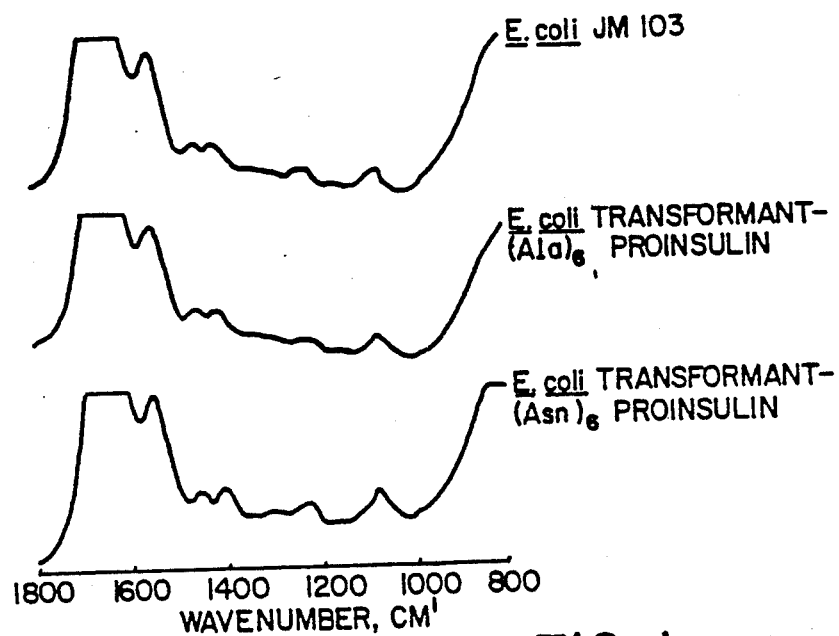
FIG. 1 shows infrared spectra of *E. coli* cells and transformed cells producing proinsulin.
Figure 2:
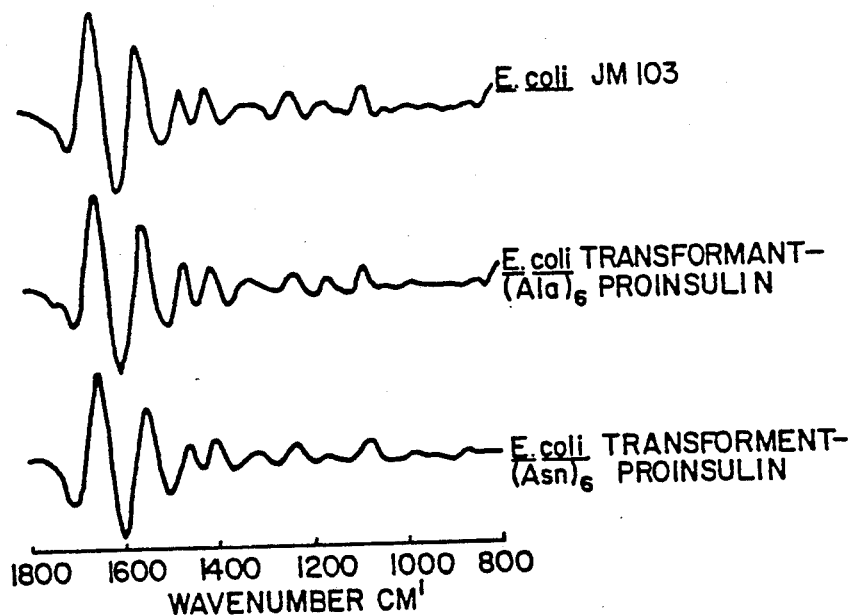
FIG. 2 shows resolution-enhanced derivative infrared spectra of *E. coli* cells and transformed cells producing proinsulin.
Figure 3:
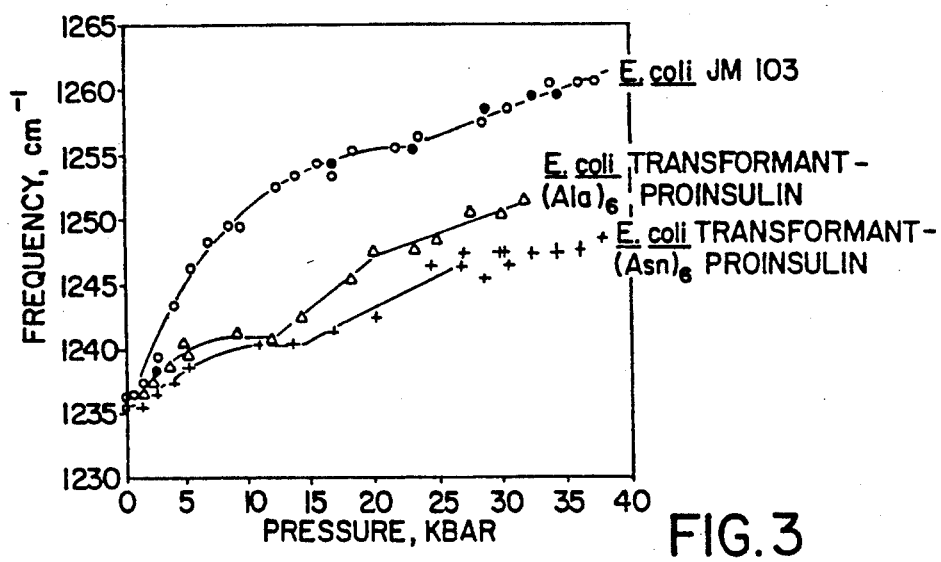
FIG. 3 is infrared spectra showing pressure dependencies of the Amide III band frequencies of *E. coli* cells and transformed cells producing proinsulin.

FIG. 1 shows the infrared spectra of *E. coli* strain JM103(A) and two transformants containing aggregates of proinsulin fused with either a $(Ala)_6(B)$ or a $(Asn)_6(C)$ leader. The corresponding resolution-enhanced infrared spectra have been obtained by third power derivative using a breakpoint of 0.1 in the Fourier domain as shown in FIG. 2. Most of the infrared bands in the frequency region shown in FIGS. 1 and 2 are due to the vibration modes of the skeletal amide groups and the side chain groups of the bacterial proteins with the exception of the band at 1664 cm$^{-1}$ which is due to the bending mode of water molecules. It is clear from FIGS. 1 and 2 that the main features in the infrared spectra of the proinsulin-producing transformants are generally identical to that of the *E. coli* host strain, although subtle differences in the infrared spectra can still be observed among these samples. However, as shown in FIG. 3, the effect of pressure on specific spectral parameters of the proinsulin-producing transformants is quite different from that of the *E. coli* host JM103. The pressure-induced frequency shift of the amide III band (1235 cm$^1$) of the proinsulin-producing transformants is much smaller than that of the *E. coli* host JM103 (FIG. 3).

The amide III band in proteins is mainly due to the C-N-H in-plane bending vibration and its location in the infrared spectrum is determined by the conformational structure of protein molecules. For a β-sheet structure this band is generally found in the frequency region 1220-1240 cm$^1$. Therefore, the band at 1235 cm$^{-1}$ observed in all *E. coli* samples at ambient conditions are due to the amide III band of the β-sheet portions of the cellular proteins. Frequency of the same band is affected by the strength of the hydrogen bond on the NH group. Obviously, the hydrogen bonds in the bacterial proteins of the *E. coli* JM103 and the proinsulin-producing transformants responds differently to identical external pressure as demonstrated by variation of the frequency of the amide III band.

The large difference in the pressure shift of the amide III band, between the *E. coli* cells and the transformants overproducing proinsulin thus provides an efficient technique for on-line monitoring of the production of recombinant proteins in *E. coli*. A decrease in this frequency from 1250 cm$^{-1}$ to 1240 cm$^{-1}$ at 10 kbar, which can be measured within 10 minutes, indicates that the genes in the *E. coli* sample have reached the maximum expression and the recombinant protein has been accumulated as aggregates.

Example 2

For this test, *E. coli* JM103 cells were transformed by plasmid pTLY.23-5 to produce T4-lysozyme (1-78), a short T4-lysozyme analog constituted by the first 78 amino acid residues, as an aggregate.

Figure 4:
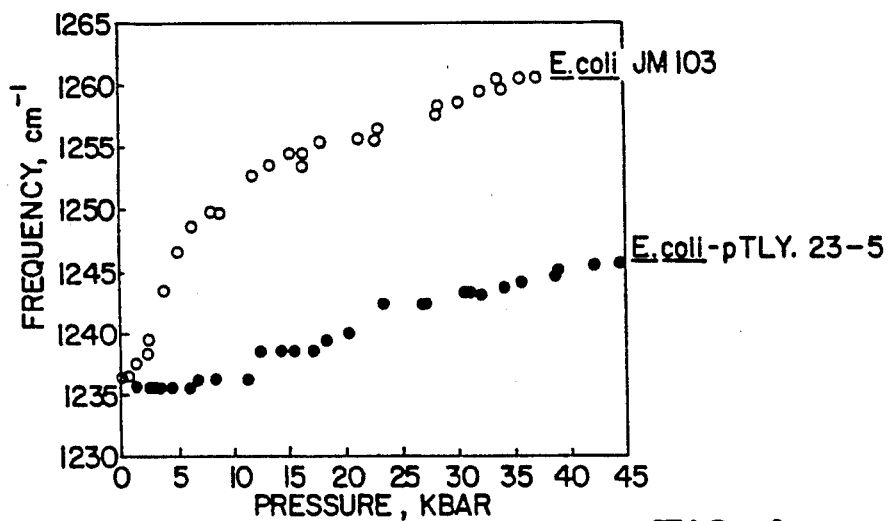
FIG. 4 shows the pressure dependencies of the Amide III band frequencies of *E. coli* cells and transformed cells producing T4-lysozyme (1-78)

The culture medium was centrifuged to obtain *E. coli* pellets and these were subjected to infrared spectrographic analysis with pressure-induced shift. FIG. 4 shows the results at the amide III band (1235 cm$^{-1}$ at atmospheric pressure of 1 bar). When the pressure was increased, the frequency of the amide III band of the JM103 control and the lysozyme-producing *E. coli* changed significantly. Thus, the high pressure IR clearly distinguished between the producing and non-producing cells.

Example 3

*E. coli* JM103 cells were transformed by plasmid pTLY.10, to produce intact T4-lysozyme of 164 amino acid residues as a soluble protein.

Figure 5:
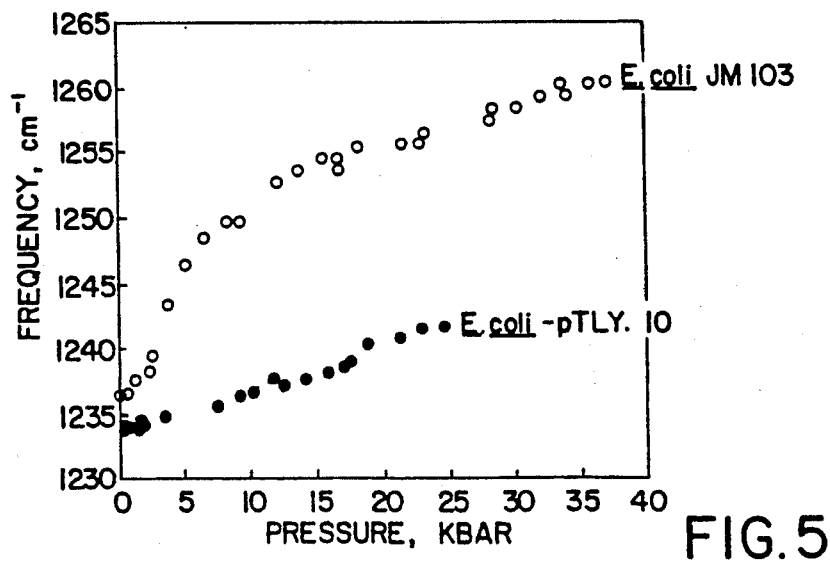
FIG. 5 shows the pressure dependencies of the Amide III band frequencies of *E. coli* producing soluble intact lysozyme and untransformed *E. coli* cells.

This soluble material was subjected to infrared spectroscopic analysis with pressure induced shift and the results are shown in FIG. 5. Here again a very distinct shift was noted between the control JM103 and the *E. coli* producing the soluble intact lysozyme.

We claim:

1. A process for monitoring the production of recombinant proteins synthesized in *E. coli* which comprises retaining a sample or produced recombinant protein in a pressure holder, applying a high pressure to the sample in the holder, subjecting the pressurized sample to infrared spectroscopic analysis at a selected infrared band and comparing the pressure induced infrared frequency shift of this band obtained against the pressure-induced shift of a standard at the pressure used, thereby determining the completeness of the protein production.

2. A process according to claim 1 wherein the sample being tested contains powdered quartz, with the pressure on the sample being measured as a function of the infrared absorption band of quartz.

3. A process according to claim 1 wherein the frequency is the amide III band.

4. A process according to claim 1 wherein the protein is in soluble form.

5. A process according to claim 1 wherein the protein is in aggregate bodies.

6. A process according to claim 1 wherein the protein is accumulated in cytoplastic inclusion bodies.

7. A process according to claim 1 wherein the protein is proinsulin.

8. A process according to claim 1 wherein the protein is lysozyme.

* * * * *